United States Patent [19]

Himmele et al.

[11] Patent Number: 4,914,133
[45] Date of Patent: Apr. 3, 1990

[54] AMINO COMPOUNDS AND FUNGICIDES CONTAINING THEM

[75] Inventors: Walter Himmele, Walldorf; Hubert Sauter, Mannheim; Hardo Siegel, Speyer; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 181,503

[22] Filed: Apr. 14, 1988

[30] Foreign Application Priority Data

Apr. 25, 1987 [DE] Fed. Rep. of Germany ....... 3713934

[51] Int. Cl.$^4$ ................................................. A01N 33/02
[52] U.S. Cl. ..................................... 514/654; 514/655; 564/374; 564/383; 564/391; 564/384
[58] Field of Search ................ 514/654, 655; 564/374, 564/383, 384, 391

[56] References Cited

U.S. PATENT DOCUMENTS

| | | | |
|---|---|---|---|
| 4,202,894 | 5/1980 | Pfiffner | 514/239 |
| 4,487,965 | 12/1984 | Himmele et al. | 514/659 |
| 4,721,786 | 1/1988 | Weissmuller et al. | 71/88 |

FOREIGN PATENT DOCUMENTS 0224163 11/1986 European Pat. Off. .
2825961 6/1978 Fed. Rep. of Germany .
988630 4/1965 United Kingdom .

Primary Examiner—Douglas W. Robinson
Assistant Examiner—Zohreh A. Fay
Attorney, Agent, or Firm—Oblon, Spivak, McClelland, Maier & Neustadt

[57] ABSTRACT

Amino compounds of the formula

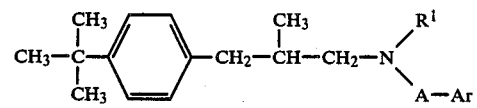

where $R^1$ is alkyl, A is alkylene or alkenylene, and Ar is aryl, and their acid addition salts, and fungicides containing these compounds.

5 Claims, No Drawings

AMINO COMPOUNDS AND FUNGICIDES CONTAINING THEM

The present invention relates to amino compounds, fungicides containing them, and methods of combating fungi with these compounds.

It is known to use N-tridecyl-2,6-dimethylmorpholine (DE 1 164 152) and 3-p-isopropylphenyl-2-methyl-1-(N,N-dialkylamino)-propanes (DE 2 825 961) and N-(3-[tert-butylphenyl]-2-methylpropyl)-2,6-dimethylmorpholine (DE 2 752 135) as fungicides. However, their fungicidal action is not completely satisfactory.

We have now found that amino compounds of the formula

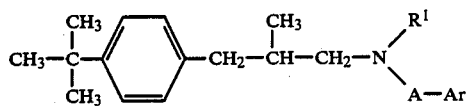

where $R^1$ is alkyl of up to 3 carbon atoms, A is alkylene of up to 4 carbon atoms or alkenylene of up to 3 carbon atoms, and Ar is substituted or unsubstituted aryl, and their acid addition salts, have a good fungicidal action which is better than that of prior art fungicides.

Examples of $R^1$ are methyl, ethyl, propyl and isopropyl.

Examples of A are methylene, ethylene, propylene, butylene and propylene.

Examples of A—Ar are phenylalkyl, e.g., phenylmethyl (benzyl), 2-phenylethyl, 1-phenylethyl, 3-phenylpropyl, 3-phenyl-2-methylpropyl, 2-phenylpropyl, 3-phenyl-2-propyl, indan-1-ylmethyl or the radical

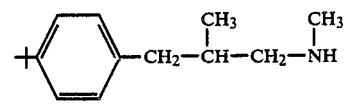

or the radical

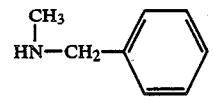

Examples of meanings for Ar are phenyl and indanyl.

The phenyl radical is unsubstituted or substituted by alkyl of up to 4 carbon atoms. The alkylene radical is unsubstituted or substituted by alkyl of up to 2 carbon atoms. Acid addition salts are those with inorganic or organic acids, e.g., hydrohalo acids (hydrochloric acid, hydrobromic acid), sulfuric acid, acetic acid and dodecylbenzenesulfonic acid.

The compounds are produced for example by reacting a compound of the formula

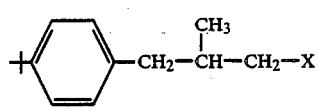

where X is a leaving group such as chlorine, bromine —OSO₂—CH₃ or

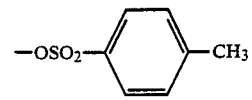

with an amine of the formula

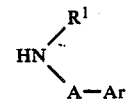

They may also be produced by reaction of amines with carbonyl compounds by aminating hydrogenation, e.g., compound 2 may be prepared by reaction of benzaldehyde—either under catalytic hydrogenation conditions or with formic acid—with an amine of the formula

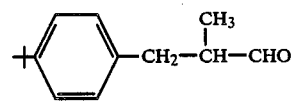

or by reaction of an amine of the formula

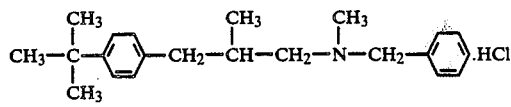

with a carbonyl compound of the formula

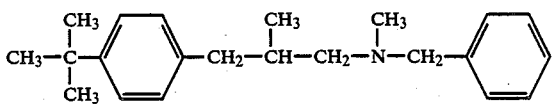

Reaction of 3-(tert-butylphenyl)-2-methyl-propyl-1-chloride with N-methyl-N-benzylamine gives the compound CH₃—C(CH₃)₂(CH₃)—[C₆H₄]—CH₂—CH(CH₃)—CH₂—N(CH₃)—CH₂—[C₆H₅]·HCl having a melting point of 170° C. (compound no. 10).

Addition of alkali to this compound gives the compound

CH₃—C(CH₃)₂(CH₃)—[C₆H₄]—CH₂—CH(CH₃)—CH₂—N(CH₃)—CH₂—[C₆H₅]

having a boiling point of (5) of 180°–190° C. (compound no. 2).

MANUFACTURING EXAMPLE 1

3-(p-tert-butylphenyl)-2-methylpropyl-(N-methyl-N-benzylamine)

876 g (4 mol) of 3-(p-tert-butylphenyl)-2-methyl-1-methylaminopropane is introduced into a 4-liter stirred flask. While stirring, 424 g of benzaldehyde is dripped in. The mixture turns milky and heats up slightly. 400 g of toluene is added as entrainer.

The mixture is heated to boiling (140° to 188° C.), the water is removed from the distillate and the toluene is recycled to the mixture. A total of 55 g (3.05 mol) of water is removed. This takes 3 hours under these conditions.

To reduce the corresponding enamine, 193 g of 98 wt% strength formic acid is dripped in at a temperature of 125° to 140° C. and over a period of 4.5 hours. $CO_2$ is evolved.

The amine is isolated by fractional distillation (b.p.(5) 180°–190° C.). 591 g of the amine is isolated, corresponding ot a yield of 48%.

MANUFACTURING EXAMPLE 2

The amine of Example 1 is prepared by reaction of 3-(p-tert-butylphenyl)-2-methylpropanal with methylbenzylamine and formic acid as reducing agent. The amine yield is 63%. The amine distils over at 5 mbar between 180° and 190° C. In both cases, the purity of the amine is greater than 97%.

MANUFACTURING EXAMPLE 3

3-(p-tert-butylphenyl)-2-methyl-1-(N-methyl-N-2-phenylpropyl-1)-propylamine (compound no. 3)

In the manner described in Example 2, 1201 g (8 mol) of 2-phenylpropylamine is reacted to the enamine with 1632 g of 3-(p-tert-butylphenyl)-2-methylpropanal. The reduction is carried out at 122° to 140° C. with formic acid. There is obtained 2082 g of amine as a 96% strength product having a boiling range of 0.3 mbar of 136° to 140° C. The yield is 78%.

The following compounds are obtained analogously:

TABLE 1

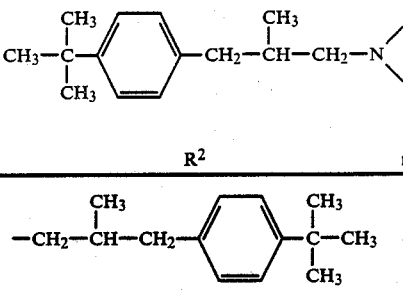

| Compound No. | $R^1$ | $R^2$ | mp °C. | bp mbar/°C. |
|---|---|---|---|---|
| 1 | $CH_3$ | 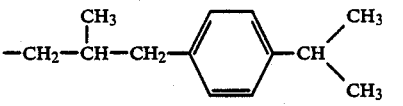 | | 0.3/195–200 |
| 2 | $CH_3$ | benzyl | | 5/180–190 |
| 3 | $CH_3$ | 2-phenyl-prop-1-yl | | 0.3/136–140 |
| 4 | $CH_3$ | 3-phenyl-but-1-yl | | 5/207–220 |
| 5 | $CH_3$ | indan-1-ylmethyl | | 5/178–196 |
| 6 | $CH_3$ | 3-phenyl-2-propen-1-yl | | 5/210–215 |
| 7 | $CH_3$ | 3-phenyl-prop-1-yl | | 0.3/165–167 |
| 8 | $CH_3$ | 1-phenyl-ethyl | | 5/180–185 |
| 9 | $CH_3$ | | | 0.3/190–195 |
| 10 | $CH_3$ | benzyl.hydrochloride | 170 | |
| 11 | $CH_3$ | 2-phenyl-prop-1-yl.hydrochloride | 180 | |
| 12 | $CH_3$ | 3-phenyl-but-1-yl.hydrochloride | 198 | |
| 13 | $CH_3$ | indan-1-ylmethyl.hydrochloride | | |
| 14 | $CH_3$ | 3-phenyl-2-propen-1-yl-hydrochloride | 195 | |
| 15 | $CH_3$ | 3-phenyl-prop-1-yl.hydrochloride | 158 | |
| 16 | $CH_3$ | benzyl.hydrobromide | 156 | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops of their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes, Fusarium and Verticillium species in various plants.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, toluene), chlorinated aromatics (e.g., chlorobenzenes), paraffins (e.g., crude oil fractions), alcohols (e.g., methanol, butanol), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably 0.5 to 90, wt% of active ingredient. The application rates are from 0.02 to 3 kg or more of active ingredient per hectare, depending on the type of effect desired. The novel compounds may also be used for protecting materials, e.g., on *Paecilomyces variotii.*

Some of the novel compounds have a very good action on human-pathogenic fungi, such as *Trichophyton mentagrophytes* and *Candida albicans.*

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 2 is mixed with 10 parts by weight of N-methyl-α-pyrrolidone. A mixture is obtained which is suitable for application in the form of very fine drops.

II. 20 parts by weight of compound no. 4 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 6 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 7 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 8 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 21 is intimately mixed with 97 parts by weight of particulate kaolin. A dust is obtained containing 3% by weight of the active ingredient.

VII. 30 parts by weight of compound no. 23 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 8 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 4 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;

heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

In the following experiments, the prior art compound N-tridecyl-2,6-dimethylmorpholine (A) (disclosed in DE 11 64 152) was used for comparison purposes.

USE EXAMPLE 1

Action on wheat brown rust

Leaves of pot-grown wheat seedlings of the "Jubilar" variety were dusted with spores of brown rust (*Puccinia recondita*). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results of this experiment show that for example compounds 3, 4, 6, 7, 8, 10, 11, 12 and 15 had, when employed as 0.05 wt% aqueous spray liquors, a better fungicidal action (97%) than prior art active ingredient A (70%).

USE EXAMPLE 2

Action on cucumber mildew

Leaves of pot-grown cucumber seedlings of the "Chinesische Schlange" variety were sprayed at the two-leaf stage with an aqueous conidial suspension of cucumber mildew. After about 20 hours, these plants were sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 70 to 80%. The extent of fungus spread was determined 21 days after inoculation.

The results obtained show that compounds 5, 6, 7, 10, 12, 13, 14 and 15, applied as a 0.05% spray liquor, had a better fungicidal action (97%) than prior art active ingredient A (70%).

We claim:

1. Amino compounds of the formula

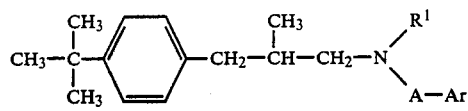

where $R^1$ is alkyl of up to 3 carbon atoms, A is alkylene of up to 4 carbon atoms or alkenylene of up to 3 carbon atoms, and Ar is phenyl or indan-1-yl, or substituted phenyl or indan-1-yl, and acid addition salts thereof.

2. A fungicidal agent containing a carrier and an amino compound of the formula

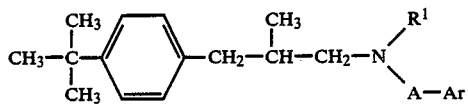

where $R^1$ is alkyl of up to 3 carbon atoms, A is alkylene of up to 4 carbon atoms or alkenylene of up to 3 carbon atoms, and Ar is phenyl or indan-1-yl, or substituted phenyl or indan-1-yl, or an acid addition salt thereof.

3. A process for combating fungi, wherein the fungi, or the materials, plants, soil or seed threatened by fungus attack are treated with a fungicidally effective amount of an amino compound of the formula

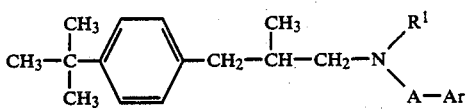

where $R^1$ is alkyl of up to 3 carbon atoms, A is alkylene of up to 4 carbon atoms or alkenylene of up to 3 carbon atoms, and Ar is phenyl or indan-1-yl, or substituted phenyl or indan-1-yl, or an acid addition salt thereof.

4. An amino compound as set forth in claim 1, where $R^1$ is methyl and A—Ar is benzyl.

5. An amino compound as set forth in claim 1, where $R^1$ is methyl and A—Ar is 3-phenylprop-1-yl.

* * * * *